(12) United States Patent
Guttman et al.

(10) Patent No.: US 11,078,480 B2
(45) Date of Patent: Aug. 3, 2021

(54) HIGH-THROUGHPUT IDENTIFICATION OF INTERMOLECULAR INTERACTIONS

(71) Applicant: California Institute of Technology, Pasadena, CA (US)

(72) Inventors: Mitchell Guttman, Los Angeles, CA (US); Sofia A. Quinodoz, Pasadena, CA (US); Mario R. Blanco, Los Angeles, CA (US); Devdoot Majumdar, Colchester, VT (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 16/575,124

(22) Filed: Sep. 18, 2019

(65) Prior Publication Data

US 2020/0087657 A1  Mar. 19, 2020

Related U.S. Application Data

(60) Provisional application No. 62/733,510, filed on Sep. 19, 2018.

(51) Int. Cl.
*C12N 15/10* (2006.01)
*G01N 33/53* (2006.01)
*G01N 33/68* (2006.01)

(52) U.S. Cl.
CPC ..... *C12N 15/1055* (2013.01); *C12N 15/1065* (2013.01); *G01N 33/5308* (2013.01); *G01N 33/6845* (2013.01)

(58) Field of Classification Search
CPC ............ C12N 15/1055; C12N 15/1065; G01N 33/5308; G01N 33/6845
See application file for complete search history.

(56) References Cited

U.S. PATENT DOCUMENTS

| 7,238,478 B2 | 7/2007 | Braman et al. | |
|---|---|---|---|
| 2019/0145982 A1* | 5/2019 | Chee | G01N 33/6824 435/6.11 |
| 2019/0187156 A1 | 6/2019 | Quinodoz | |

FOREIGN PATENT DOCUMENTS

WO WO 2012/041802 A1 4/2012

OTHER PUBLICATIONS

B. A. R. Williams, J. C. Chaput, Synthesis of peptide-oligonucleotide conjugates using a heterobifunctional crosslinker. Curr. Protoc. Nucleic Acid Chem. (2010), , doi:10.1002/0471142700. nc0441s42.

Blackstock, D. et al., Halo-tag mediated self-labeling of fluorescent proteins to molecular beacons for nucleic acid detection, ChemCommun. 2014, vol. 50, pp. 13735-13738.
C. Keryer-Bibens, C. Barreau, H. B. Osborne, Tethering of proteins to RNAs by bacteriophage proteins. Biol. Cell (2008), doi:10.1042/BC20070067.
D. Lipovsek, A. Plückthun, In-vitro protein evolution by ribosome display and mRNA display. J. Immunol. Methods (2004), , doi:10. 1016/j.jim.2004.04.008.
D. S. Wilson, A. D. Keefe, J. W. Szostak, The use of mRNA display to select high-affinity protein-binding peptides. Proc. Natl. Acad. Sci. (2001), doi:10.1073/pnas.061028198.
Kozlov, I.A. et al., Efficient Strategies for the Conjugation of Oligonucleotides to Antibodies Enabling Highly Sensitive Protein Detection, Wiley InterScience, Mar. 8, 2004, pp. 621-630.
Los, G.V et al., HaloTag: A Novel Protein Labeling Technology for Cell Imaging and Protein Analysis, ACS Chemical Biology, vol. 3, No. 6, Jun. 6, 2008, pp. 373-382.
P. A. Barendt, D. T. W. Ng, C. N. McQuade, C. A. Sarkar, Streamlined protocol for mRNA display. ACS Comb. Sci. (2013), doi:10.1021/co300135r.
Pröschel, M., Probing the Potential of CnaB-type Domains for the Design of Tag/Catcher Systems, PLoS ONE 12(6):e0179740 (2017).
Solulink, "Antibody-Oligonucleotide Conjugate Preparation", Solulink. com, 4 pages.
T. T. Takahashi, R. J. Austin, R. W. Roberts, mRNA display: Ligand discovery, interaction analysis and beyond. Trends Biochem. Sci. (2003), doi:10.1016/S0968-0004(03)00036-7.
V. Singh, S. Wang, E. T. Kool, Genetically encoded multispectral labeling of proteins with polyfluorophores on a DNA backbone. J. Am. Chem. Soc. (2013), doi:10.1021/ja4004393.
Buldun et al., SnoopLigase Catalyzes Peptide-Peptide Locking and Enables Solid-Phase Conjugate Isolation, Journal of the American Chemical Society, Feb. 8, 2018, 30 pages.
Quinodoz et al. Higher-Order Inter-chromosomal Hubs Shape 3D Genome Organization in the Nucleus, Cell, Jul. 26, 2018. vol. 174, p. 744-757, 39 pages.
Tan et al., Kinetic Controlled Tag-Catcher Interactions for Directed Covalent Protein Assembly, PLOS one, Oct. 26, 2016, 15 pages.
Veggiani et al., Programmable Polyproteams built using twin peptide superglues, PNAS, Feb. 2, 2016, 6 pages, vol. 113 No. 5.
Williams et al. Synthesis of Peptide-Oligonucleotide Conjugates Using a Heterobifunctional Crosslinker, Current Protocols in Nucleic Acid Chemistry Chapter: Unit 4.41, Sep. 2010, 35 pages.
Zakeri et al., Spontaneous Intermolecular Amide Bond Formation between Side Chains for Irreversible Peptide Targeting, Journal of the American Chemical Society, Mar. 17, 2010 (via web), 2 pages, vol. 132 No. 13.
Zakeri et al., Peptide tag forming a rapid covalent bod to a protein, through engineering a bacterial adhesin, PNAS, Feb. 24, 2012, 8 pages.

* cited by examiner

*Primary Examiner* — Robert H Havlin
(74) *Attorney, Agent, or Firm* — Knobbe, Martens, Olson & Bear, LLP (57) ABSTRACT

Methods of detecting an interaction between a macromolecule and an interaction partner are described. Kits are also described.

18 Claims, 5 Drawing Sheets
Specification includes a Sequence Listing.

HIGH-THROUGHPUT IDENTIFICATION OF INTERMOLECULAR INTERACTIONS

INCORPORATION BY REFERENCE TO ANY PRIORITY APPLICATIONS

This application claims the benefit of U.S. Provisional App. No. 62/733,510, filed Sep. 19, 2018, which is incorporated by reference in its entirety herein. Any and all applications for which a foreign or domestic priority claim is identified in the Application Data Sheet as filed with the present application are hereby incorporated by reference under 37 CFR 1.57.

STATEMENT REGARDING FEDERALLY SPONSORED R&D

This invention was made with government support under Grant No(s). OD012190, DA040612, and HL130007 awarded by the National Institutes of Health. The government has certain rights in the invention.

REFERENCE TO SEQUENCE LISTING, TABLE, OR COMPUTER PROGRAM LISTING

The present application is being filed along with a Sequence Listing in electronic format. The Sequence Listing is provided as a file CALTE145ASEQLIST.txt, created and last modified on Sep. 18, 2019, which is 1,500 bytes in size. The information in the electronic format of the Sequence Listing is incorporated herein by reference in its entirety.

BACKGROUND

Almost all detection methods for proteins utilize affinity reagents such as antibodies and aptamers. Yet, there are still a limited number of high-quality affinity reagents for most proteins. A reason for this is that conventional methods for screening libraries of molecules that bind to proteins, or that interfere with protein interactions, are typically low-throughput, labor intensive, and expensive. Thus, the ability to perform high-throughput screening of affinity reagents for specific proteins has conventionally been limited, and has conventionally resulted in a bottle-neck in the numbers of affinity reagents that are available. As an example, a complex library of in vitro generated affinity reagents (>$10^{13}$ combinations) may be readily generated, yet evaluating which sequence binds a specific protein through individual interaction assays would involve billions of individual assays, which is not amendable to conventional screening platforms.

FIELD

Some embodiments herein relate to detection of molecular interactions, for example, protein-protein, protein-DNA, protein-RNA, and protein-small molecule interactions.

SUMMARY

In some embodiments, a method of detecting an interaction between a macromolecule and an interaction partner is described. The detecting method can comprise obtaining a composition comprising macromolecules and candidate interaction partners. The detecting method can comprise performing two or more iterations of split-and-pool barcoding, in which each iteration comprises (i) randomly distributing the composition into a plurality of partitions in fluid isolation from each other. The detecting method can further comprise (ii) in the partitions, barcoding the macromolecules and candidate interaction partners with a combinatorial barcode unit, in which, within each partition, the macromolecules and candidate interaction partners are barcoded with the same combinatorial barcode unit, and in which macromolecules and candidate interaction partners of different partitions receive different combinatorial barcode units from each other. The detecting method can further comprise (iii) pooling the barcoded macromolecules and candidate interaction partners comprising the combinatorial barcode units from the different partitions into a single composition. After the two or more iterations of split-and-pool barcoding, each macromolecule and candidate interaction partner can comprise a combinatorial barcode comprising two or more combinatorial barcode units, in which each combinatorial barcode unit corresponds to an iteration of split-and-pool-barcoding. The detecting method can further comprise obtaining identifying information from the combinatorial barcodes of the macromolecules and candidate interaction partners, in which the identifying information permits detecting association between a macromolecule and candidate interaction partner through the two or more iterations of split-and-pool barcoding. A probability of a bona fide interaction between an associated macromolecule and candidate interaction partner can be proportional to the number of iterations of split-and-pool barcoding. In the detecting method of some embodiments, each macromolecule is a protein, and each macromolecule comprises an identifier barcode comprising an polynucleotide comprising a coding sequence of the macromolecule, for example an mRNA encoding the macromolecule. The identifier barcode may further comprise a covalent polypeptide tag fused to the polynucleotide, and the protein may further comprise a counterpart polypeptide sequence covalently bound to the covalent polypeptide tag. In the detecting method of some embodiments, the counterpart polypeptide sequence is disposed at an N-terminal region of the macromolecule (protein). The detecting method of some embodiments further comprises fusing the covalent polypeptide tag to the polynucleotide encoding the macromolecule, and translating the polynucleotide in vitro, thus producing the macromolecule comprising the counterpart polypeptide sequence disposed at an N-terminal portion of the macromolecule. The detecting method may further comprise covalently binding the polypeptide tag to the counterpart polypeptide sequence, thus making the macromolecule comprising the identifier barcode. Examples of covalent polypeptide tag and counterpart polypeptide sequences suitable for detecting methods herein include, but are not limited to, a split CnaB protein; or a Spytag and SpyCatcher; or Isopeptag and pilin-C; or SnoopTag and SnoopCatcher; or DogTag and SnoopTagJr; or SdyTag and SdyCatcher, or a combination of two or more of any of the listing pairs. For example, the covalent polypeptide tag and counterpart polypeptide sequences may comprise a Spytag and SpyCatcher; or Isopeptag and pilin-C; or SnoopTag and SnoopCatcher; or DogTag and SnoopTagJr; or SdyTag and SdyCatcher, or a combination of two or more of any of the listing pairs. It will be appreciated that the listed pairs specifically form covalent bonds with each other, and thus either member of the listed pairs may serve as "polypeptide tag" in accordance with detecting methods and kits of some embodiments herein, provided that the other pair member serves as the "counterpart polypeptide sequence." Thus, for example, a Spytag may serve as a "polypeptide tag" whicle a SpyCatcher serves as a "counterpart polypeptide sequence," or SpyCatcher may serve as a "polypeptide tag" while a SpyTag serves as a "counterpart polypeptide sequence. In the detecting method of some embodiments, the covalent polypeptide tag is fused to the polynucleotide via a HUH protein, SMCC linkage, or RepB replicase. In the detecting method of some embodiments, the identifier barcode further comprises a random oligonucleotide barcode or at least 5 nucleotides. In the detecting method of some embodiments, the identifier barcode further comprises a terminal single-stranded handle sequence. Each combinatorial barcode unit can comprise a terminal single-stranded complementary to the terminal handle sequence. The barcoding can comprises permitting the terminal single-stranded handle sequences to anneal to the terminal single-stranded complements, and ligating the terminal handle sequences to the terminal complements. In the detecting method of some embodiments, the combinatorial barcode units comprise oligonucleotides, and different oligonucleotide sequences differentiate different combinatorial barcode units from each other. In the detecting method of some embodiments, the combinatorial barcode units comprise detectable moieties, and different detectable moieties differentiate different combinatorial barcode units from each other. In the detecting method of some embodiments, obtaining sequence information from the combinatorial barcodes of the macromolecules and candidate interaction partners further comprises obtaining sequence information of the coding sequence of the macromolecule. In the detecting method of some embodiments, the macromolecules are of a library of in vitro translated polypeptides. In the detecting method of some embodiments, the macromolecules are selected from the group consisting of proteins, RNA binding proteins, antigen binding proteins, antibodies or fragments thereof, scFvs, nanobodies, and aptamers, or a combination of two or more of any of the listed items. In the detecting method of some embodiments, the candidate interaction partners are selected from the group consisting of: proteins, peptides, RNAs, DNAs, and small molecules, or a combination of two or more of any of the listed items. In the detecting method of some embodiments, the composition comprises at least $10^3$, different macromolecules and at least $10^3$ different candidate interaction partners. In the detecting method of some embodiments, the composition comprises at least $10^6$, different macromolecules and at least $10^6$ different candidate interaction partners. In the detecting method of some embodiments, a macromolecule associates with a first candidate interaction partner through the split-and-pool barcoding, and a second candidate interaction partner associates with the macromolecule through the split-and-pool barcoding. However, all three of the macromolecule, the first candidate interaction partner, and the second candidate interaction partner do not associate through the split-and-pool barcoding, thus indicating that the second candidate interaction partner has a probability of interfering with the association between the macromolecule and the first interaction partner. In the detecting method of some embodiments, a first macromolecule associates with a candidate interaction partner through the split-and-pool barcoding, and a second macromolecule associates with the candidate interaction partner through the split-and-pool barcoding. However, all three of the first macromolecule, the second macromolecule, and the candidate interaction partner not associating through the split-and-pool barcoding, indicates that the second macromolecule has a probability of interfering with the association between the macromolecule and the first interaction partner. The detecting method of some embodiments, comprises at least 3 iterations of split-and-pool barcoding, for example at least 3, 4 5, 6 7, 8, 9, 10, 11, 12, 13, 14, 15, 16, 17, 18, 19, 20, 21, 22, 23, 24, 25, 25, 27, 28, 29, or 30 iterations, including ranges between any two of the listed values, for example, 3-5 iterations, 3-10 iterations, 3-15 iterations, 3-25 iterations, 3-30 iterations, 5-10 iterations, 5-15 iterations, 5-25 iterations, 5-30 iterations, 7-10 iterations, 7-15 iterations, 7-25 iterations, 7-30 iterations, 10-15 iterations, 10-25 iterations or 10-30 iterations. For any detecting method described herein, the macromolecules may be of a library of in vitro translated polypeptides.

In some embodiments, a kit is described. The kit can comprise a vector comprising an insertion site and counterpart polypeptide coding sequence, in which the insertion site is arranged to place a protein coding sequence in frame with the counterpart polypeptide coding sequence without any intervening stop codon, upon the insertion of the protein coding sequence in the insertion site. The kit can further comprise a covalent polypeptide tag, in which the covalent polypeptide tag and the counterpart polypeptide sequence are configured to specifically covalently bind to each other. The kit can further comprise at least two different combinatorial barcode units. In the kit of some embodiments, the covalent polypeptide tag further comprises a protein that binds to a polynucleotide. In the kit of some embodiments, the protein that binds to a polynucleotide is selected from the group consisting of a HUH protein, a SMCC linkage, or a RepB replicase, or a combination of two or more of the listed items. In the kit of some embodiments, the different combinatorial barcode units comprise oligonucleotides having different sequences, and/or the different combinatorial barcode units comprise different fluorophores.

DETAILED DESCRIPTION

Described herein are methods and kits for high-throughput detection of molecular interactions, for example, protein-protein, protein-DNA, protein-RNA, and protein-small molecule interactions. The detecting methods of some embodiments comprise multiple iterations of split-and-pool barcoding. For example, the detecting methods can comprise randomly distributing a composition comprising macromolecules (such as proteins) and candidate interaction partners (such as proteins, peptide, RNA, DNA, and/or small molecules) among multiple partitions. The partitions can be in fluid isolation from each other, for example different wells of a multi-well plate, or different chambers of a microfluidic device. The macromolecules and candidate interaction partners within each partition can be barcoded with the same combinatorial barcode unit. However, different combinatorial barcode units can be used in different partitions so that in each round, macromolecules and candidate interaction partners in different partitions receive different combinatorial barcode units. The macromolecules and candidate interaction partners from the different partitions can be re-pooled, and the partitioning, barcoding, and re-pooling can be repeated for one or more iterations. Thus, macromolecules and candidate interaction partners that interact with each other are expected to co-associate through multiple iterations of split-and-pool barcoding, and thus are expected to share the same collection and arrangement of combinatorial barcode units (which may be referred to as a "combinatorial barcode"). On the other hand, macromolecules and candidate interaction partners that do not interact are expected to assort independently of each other.

Figure 2:
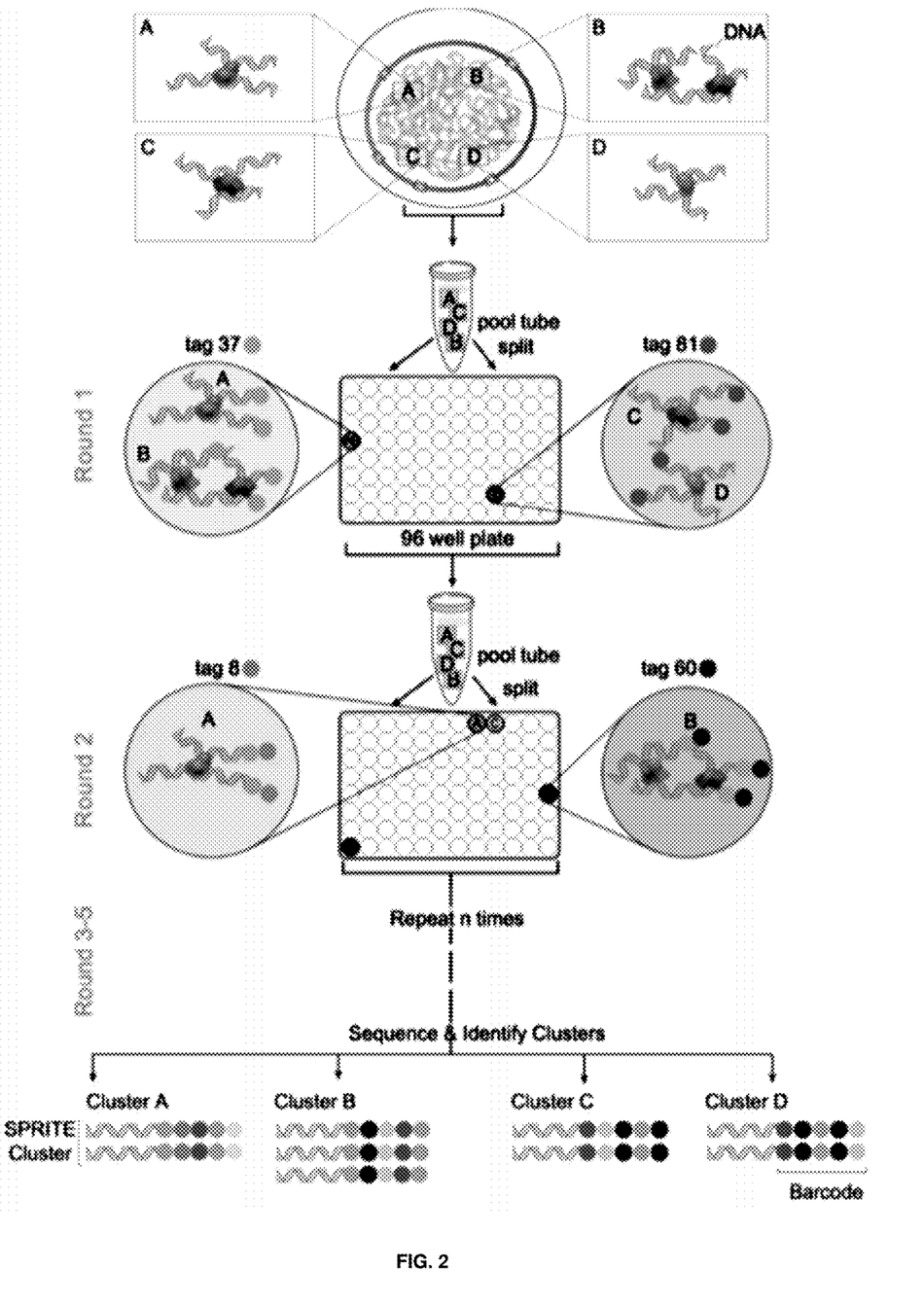
FIG. 2 is a schematic diagram illustrating a method of detecting molecular interactions using combinatorial barcoding in accordance with some embodiments herein.
Figure 3:
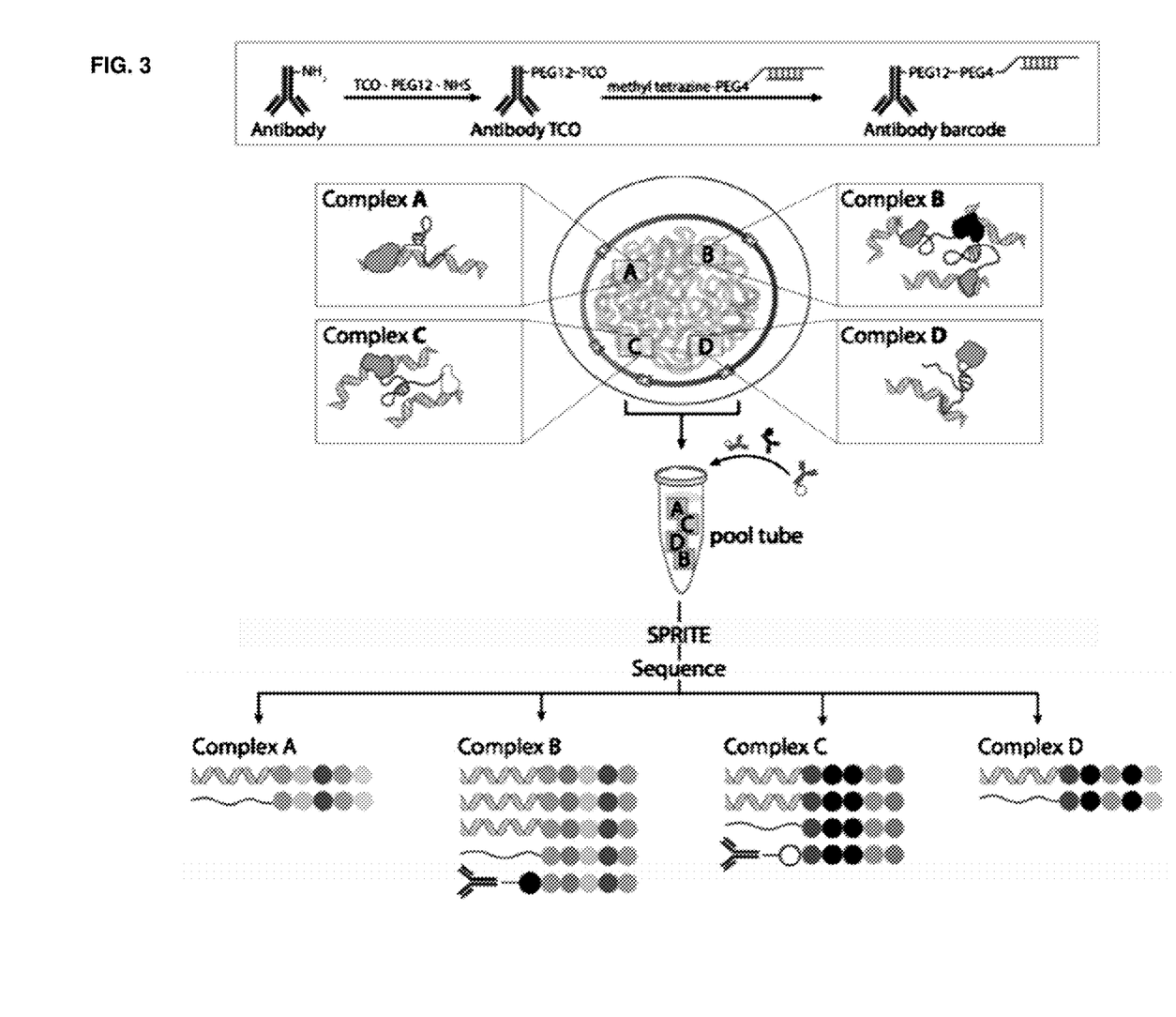
FIG. 3 is a schematic diagram illustrating a method of detecting molecular interactions between proteins or inhibitors of such interactions in accordance with some embodiments.

Detecting methods and kits of some embodiments herein permit high-throughput identification of protein-protein, protein-DNA, and protein-RNA interactions to screen highly complex libraries of billions of molecules (such as affinity reagents) that bind to proteins or libraries of molecules (including proteins, RNAs, small molecules, etc.) that interfere with protein interactions in a single experiment. The detecting methods can make use of combinatorial barcoding scheme via the addition of tags onto each affinity reagent and macromolecule (FIG. 2). Using combinatorial barcoding, molecular interactions can be converted into tag frequencies. As such, molecules that are directly interacting will assort together (and may be "associated" as described here), while fragments that are not interacting will assort independently of each other. By sorting and barcoding several times, the probability that fragments that are not interacting will obtain all of the same barcode sequences becomes exceedingly rare, while the probability of paired fragments obtaining the same barcodes remains constant. After split-and-pool barcoding, we perform high-throughput sequencing of each tagged affinity reagent, the associated macromolecule (protein, RNA, or DNA), and sequence their associated barcodes. By matching every molecule that contains a shared barcode, we can perform high-throughput screening for affinity reagents that bind to specific proteins or molecules that interfere with protein interactions In detecting methods and kits of some embodiments, molecular interactions between macromolecules (such as proteins) or inhibitors of such interactions can be identified by attaching oligonucleotide tags (such as DNA tags) during each round of split-and-pool barcoding. A nucleic acid can be directly conjugated to each macromolecule, so that it can be subsequently tagged with a combinatorial barcode units (such as a DNA barcode) in each of multiple iterations of split-and-pool barcoding, so as to combinatorially barcode the macromolecule (FIG. 3).

Macromolecules

As used herein, "macromolecule" has its customary and ordinary meaning as would be understood by one of ordinary skill in the art in view of this disclosure. It refers to a relatively large molecule such as a protein or nucleic acid such as RNA or DNA. It will be appreciated that macromolecules may be part of a larger complex, for example, a protein complex, or a protein-RNA complex, or a protein-DNA complex. Example macromolecules suitable for embodiments herein can comprise, consist essentially of, or consist of proteins, peptides, RNA binding proteins, chromatin associated proteins, enzymes, receptors, ligands, aptamers, immune cell receptors such as T cell receptors, antibodies, and antibody fragments such as Fabs, minibodies, diabodies, single chain variable fragments (scFvs), and nanobodies, or a combination of two or more of any of the listed items. In some embodiments, macromolecules are translated in vitro.

Candidate Interaction Partners

As used herein, "candidate interaction partner" has its customary and ordinary meaning as would be understood by one of ordinary skill in the art in view of this disclosure. It refers to a molecule that may interact with a macromolecule as described herein. In detecting methods and kits of some embodiments, binding between macromolecules and candidate interaction partners is detected. For example, a library of candidate interaction partners may be screened for binding to (or inhibition of complex formation for) one or more macromolecules. Examples candidate interaction partners suitable for embodiments herein can comprise, consist essentially of, or consist of proteins, peptides, DNA, RNA, and small molecules. In some embodiments, candidate interaction partners are transcribed and/or tanslated.

Barcodes

As used herein, "barcode" has its customary and ordinary meaning as would be understood by one of ordinary skill in the art in view of this disclosure. It refers to an identifier that can be associated with a molecule (such as a macromolecule or candidate interaction partner as described herein. For example, a barcode can comprise an oligonucleotide sequence, and/or a detectable moiety or combinations of detectable moieties (such as fluorophores, nanoparticles, and/or quantum dots). In some embodiments, a barcode comprises at least 5 nucleotides, for example, at least 5, 6, 7, 8, 9, 10, 11, 12, 13, 14, 15, 16, 17, 18, 19, 20, 21, 22, 23, 24, 25, 25, 27, 28, 29, or 30 nucleotides, including ranges between any two of the listed values, for example 5-10, 5-15, 5-20, 5-25, 5-30, 7-10, 7-15, 7-20, 7-25, 7-30, 10-15, 10-20, 10-25, 10-30, 12-15, 12-20, 12-25, 12-30, 15-20, 15-25, 15-30, 20-25, or 20-30 nucleotides. The length of a barcode can depend on the scale of the detecting method or kit. For example, if there are "n" different barcoded macromolecules being screened, the barcodes may have a length so that there are at least "n" different possible barcodes. Barcodes may also contain additional nucleic acid sequences, for example universal primer annealing sites, which can facilitate sequencing.

As used herein, "combinatorial barcode" has its customary and ordinary meaning as would be understood by one of ordinary skill in the art in view of this disclosure. It refers to a type of barcode that comprises multiple "combinatorial barcode units," which together yield the combinatorial barcode. For example, each combinatorial barcode unit can comprise an oligonucleotide subunit, and the sequence of the oligonucleotide subunit can provide identification information for the combinatorial barcode unit. For example, each combinatorial barcode unit can comprise an oligonucleotide subunit and a detectable moiety or combination of detectable moieties (such as a fluorophore, nanoparticle, quantum dot, or the like), which provide identifying information for the combinatorial barcode. For example, the combinatorial barcode can comprise a polyfluorophore. By way of example, a combinatorial barcode unit may comprise, consist essentially of, or consist of an oligonucleotide of at least 3, 4, 5, 6, 7, 8, 9, 10, 11, 12, 13, 14, 15, 16, 17, 18, 19, or 20 nucleotides in length, including ranges between any two of the listed values, for example, 3-8, 3-12, 3-16, or 3-20, 4-8, 4-12, 4-16, 4-20, 6-8, 6-12, 6-16, 6-20, 10-12, 10-16, or 10-20 nucleotides. The number of different combinatorial barcode units, and the length of the combinatorial barcode may depend on the scale of the detecting method or kit. For example, if there are at least "m" different partitions, the there may be at least "m" different combinatorial barcode units, so that each partition may be associated with a different combinatorial barcode unit. A combinatorial barcode may comprise at least 2 combinatorial barcode units, for example, at least 2, 3, 4, 5, 6, 7, 8, 9, 10, 11, 12, 13, 14, 15, 16, 17, 18, 19, or 20, including ranges between any two of the listed values, for example, 2-8, 2-12, 2-16, 2-20, 3-8, 3-12, 3-16, 3-20, 4-8, 4-12, 4-16, 4-20, 6-8, 6-12, 6-16, 6-20, 10-12, 10-16, or 10-20 combinatorial barcode units.

There are a number of suitable methods for attaching barcodes to macromolecules as described herein. For example, the macromolecules can be barcoded using one or more techniques, such as genetic conjugation of a nucleic acid to a polypeptide (e.g., boxB-lambdaN system (1)), mRNA display methods (2-5), or direct conjugation of nucleic acids to polypeptides (6-8)). For example, a macromolecule comprising a primary amine group (e.g., on a protein macromolecule) can be covalently bonded to a TCO-PEG-NHS moiety (such as TCO-PEG12-NHS) through covalent bonding of the NHS ester to the primary amine group. The macromolecule can then be tagged with TCO-PEG. The TCO can react with methyltetrahydrazine-PEG tagged oligonucleotide barcodes (such as methyl tetrahydrazine-PEG4) to from a macromolecule-PEG-PEG-barcode structure (such as a macromolecule-PEG12-PEG4-barcode structure) (See, e.g., FIG. 3). For example, a polynucleotide encoding a macromolecule or candidate interaction partner (such as an mRNA) can be ligated to an oligonucleotide that is coupled to a polypeptide tag (such as spy-catcher protein) via protein-oligonucleotide conjugation, such a HUH protein, SMCC linkage, or RepB replicase (See, e.g., FIGS. 4A-B). As such, the macromolecule may further comprise a protein suitable for a protein-oligonucleotide linkage, such as a HUH protein, SMCC linkage, or RepB replicase. Similarly, small molecule inhibitors can be directly tagged through conjugation of oligonucleotides to generate small molecule drug conjugates. For oligonucleotide aptamers, aptamer molecules can be directly barcoded. For example, if a macromolecule comprises an identifier barcode as described herein, combinatorial barcode units can be directly added to the oligonucleotide comprising a coding sequence of the macromolecule. Methods for coupling of oligonucleotides to proteins are also described, for example, in in Los et al., "HaloTag: a novel protein-labeling technology for cell imaging and protein analysis, ACS Chem Biol., 2008, 3:373-382; Blackstock et al., "Halo-Tag Mediated Self-Labeling of Fluorescent Proteins to Molecular Beacons for Nucleic Acid Detection," Chem. Commun., 2014, 50: 1375-13738; Kozlov et al., "Efficient Strategies for the Conjugation of Oligonucleotides to Antibodies Enabling Highly Sensitive Protein Detection," Biopolymers, 2004, 73:621; and Solulink, "Antibody-Oligonucleotide Conjugate Preparation," Solulink.com, 4 pages, each of which is incorporated by reference in its entirety herein.

There are a number of suitable methods for barcoding macromolecules and/or candidate binding partners with a combinatorial barcode unit in accordance with detecting methods and kits described herein described. For example, each combinatorial barcode unit can comprise a common "handle" oligonucleotide sequence (which may also be referred to as a "linker") and the complement of the handle, which may link combinatorial barcode units to a growing combinatorial barcode and/or each other. The handle and complement of the handle can be disposed on opposite termini of the combinatorial barcode unit. The growing combinatorial barcode can thus comprise a single-stranded complement of the handle, and each added combinatorial barcode unit can hybridize, through its handle, to the growing combinatorial barcode, while leaving a complement of the handle available for adding additional combinatorial barcode units. The hybridized combinatorial barcode unit and growing combinatorial barcode can then be ligated. In the detecting methods and kits of some embodiments, the handles and complements of the handles are single-stranded. In the detected methods and kits of some embodiments, the handles are comprised 3' ends of primers that anneal to growing ends of combinatorial barcode subunit. Upon extension, the primer can produce an oligonucleotide that comprises the sequences of the combinatorial barcode thus far, along with a handle for the additional of an additional combinatorial barcode subunit. In the detected methods of some embodiments, the handle comprises at least 4, 5, 6, 7, 8, 9, 10, 11, 12, 13, 14, or 15 nucleotides, including ranges between any two of the listed values, such as 4-8, 4-10, 4-15, 8-10, 8-15, or 10-15 nucleotides. For example, each combinatorial barcode unit, via its handle, can be ligated to the growing combinatorial barcode on a macromolecule or candidate interaction partner as described herein. Examples of combinatorial barcoding methods are described, for example, in U.S. Pre-Grant Publication No. 2019/0187156, which is incorporated by reference in its entirety herein.

Split-and-Pool Barcoding

As used herein, "split-and-pool barcoding" has its customary and ordinary meaning as would be understood by one of ordinary skill in the art in view of this disclosure. It refers to barcoding in which a composition comprising molecules is split into two or more partitions that are separate from each other. Then, the composition of each partition is barcoded so that molecules in the same partition are barcoded with the same barcode, but molecules in different partitions are barcoded with different barcodes from each other. After the barcoding, the contents of the partitions can be pooled to form a composition. The process can be repeated on this composition, so that multiple iterations of splitting, barcoding, and pooling are performed. The "partitions" refer to spaces that are in fluid isolation from each other, so that the contents of the different partitions do not mix while they are in the partitions. For example, the partitions can be separated by one or more solid barriers. Examples of partitions include, but are not limited to, wells of a multi-well plate (e.g., 96-well plate), containers such as microcentrifuge tubes, chambers of a fluid device, and the like.

After multiple iterations of split-and-pool barcoding, the macromolecules and candidate interaction partners will each comprise a combination of combinatorial barcode units. These combinations may be referred to as "combinatorial barcodes" (and accordingly, the barcoding to produce the combinatorial barcodes may be referred to as "combinatorial barcoding.").

Methods of Detecting an Interaction Between a Macromolecule and an Interaction Partner In some embodiments, methods of detecting an interaction between a macromolecule and an interaction partner are described. For conciseness, these methods may be referred to herein as "detecting methods." The detecting method can comprise obtaining a composition comprising macromolecules (for example, a library of antigen binding proteins such as nanobodies) and candidate interaction partners (for example, a library of candidate binding targets). The detecting method can comprise performing two or more iterations of split-and-pool barcoding. Each iteration of split-and-pool barcoding can comprise (i) randomly distributing the composition into a plurality of partitions in fluid isolation from each other. The iteration of split-and-pool barcoding can further comprise (ii) barcoding the macromolecules and candidate interaction partners in the partitions with a combinatorial barcode unit as described herein, so that within each partition, the macromolecules and candidate interaction partners are barcoded with the same combinatorial barcode unit. On the other hand, macromolecules and candidate interaction partners of different partitions receive different combinatorial barcode units from each other. The iteration of split-and-pool barcoding can comprise (iii), pooling, into a single composition, the barcoded macromolecules and candidate interaction partners from the different partitions and comprising the combinatorial barcode units. After the pooling, the resulting single composition can be used to perform additional iterations of the split-and-pool barcoding (comprising (i)-(iii)), so that two or more iterations are performed, for example at least 2, 3, 4 5, 6 7, 8, 9, 10, 11, 12, 13, 14, 15, 16, 17, 18, 19, 20, 21, 22, 23, 24, 25, 25, 27, 28, 29, or 30 iterations, including ranges between any two of the listed values, for example, 2-5 iterations, 2-10 iterations, 2-15 iterations, 2-25 iterations, 2-30 iterations, 5-10 iterations, 5-15 iterations, 5-25 iterations, 5-30 iterations, 7-10 iterations, 7-15 iterations, 7-25 iterations, 7-30 iterations, 10-15 iterations, 10-25 iterations or 10-30 iterations. After the two or more iterations of split-and-pool barcoding, each macromolecule and candidate interaction partner comprises a combinatorial barcode comprising two or more combinatorial barcode units (one for each iteration of the split-and-pool barcoding). The detecting method can comprise obtaining identifying information from the combinatorial barcodes of the macromolecules and candidate interaction partners, in which the identifying information permits detecting association between the macromolecules and candidate interaction partners through the two or more iterations of split-and-pool barcoding. The identifying information can comprise a frequency of common combinatorial barcode unites between the macromolecule and the candidate interaction partner. A macromolecule and candidate interaction partner that have the same combinatorial barcode, or substantially similar combinatorial barcodes may be considered to "associate" or "be associated." As used herein, a "substantially similar" combinatorial barcode refers to a combinatorial barcode that indicates that the macromolecule and candidate interaction partner were present in the same partition in multiple iterations of split-and-pool barcoding, such that there is less than a 1% probability that the similarities in combinatorial barcodes is attributable to random association through the multiple iterations of split-and-pool barcoding, for example, less than 1%, 0.5%, 0.1%, 0.01%, or 0.001% probability. The probability of random association can be calculated based on the number of iterations of split-and-pool barcoding and the number of partitions, and/or empirically, for example based on a particular macromolecule and candidate binding partner pair known to not interact. It is contemplated that a probability of a bona fide interaction between the macromolecule and a candidate interaction partner is proportional to the number of iterations of split-and-pool barcoding. For example, there is a greater degree of probability of a bona fide interaction between a macromolecule and candidate interaction partner that co-assort through eight iterations of split-and-pool barcoding as described herein, than there is for a macromolecule and candidate interaction partner that co-assort through two iterations of split-and-pool barcoding. It is further contemplated that a probability of a bona fide interaction between the macromolecule and a candidate interaction partner is proportional to the number of partitions. For example, there is a greater degree of probability of a bona fide interaction between a macromolecule and candidate interaction partner that co-assort when a composition is divided among 96 partitions than there is when the composition is divided among two partitions.

Figure 1:
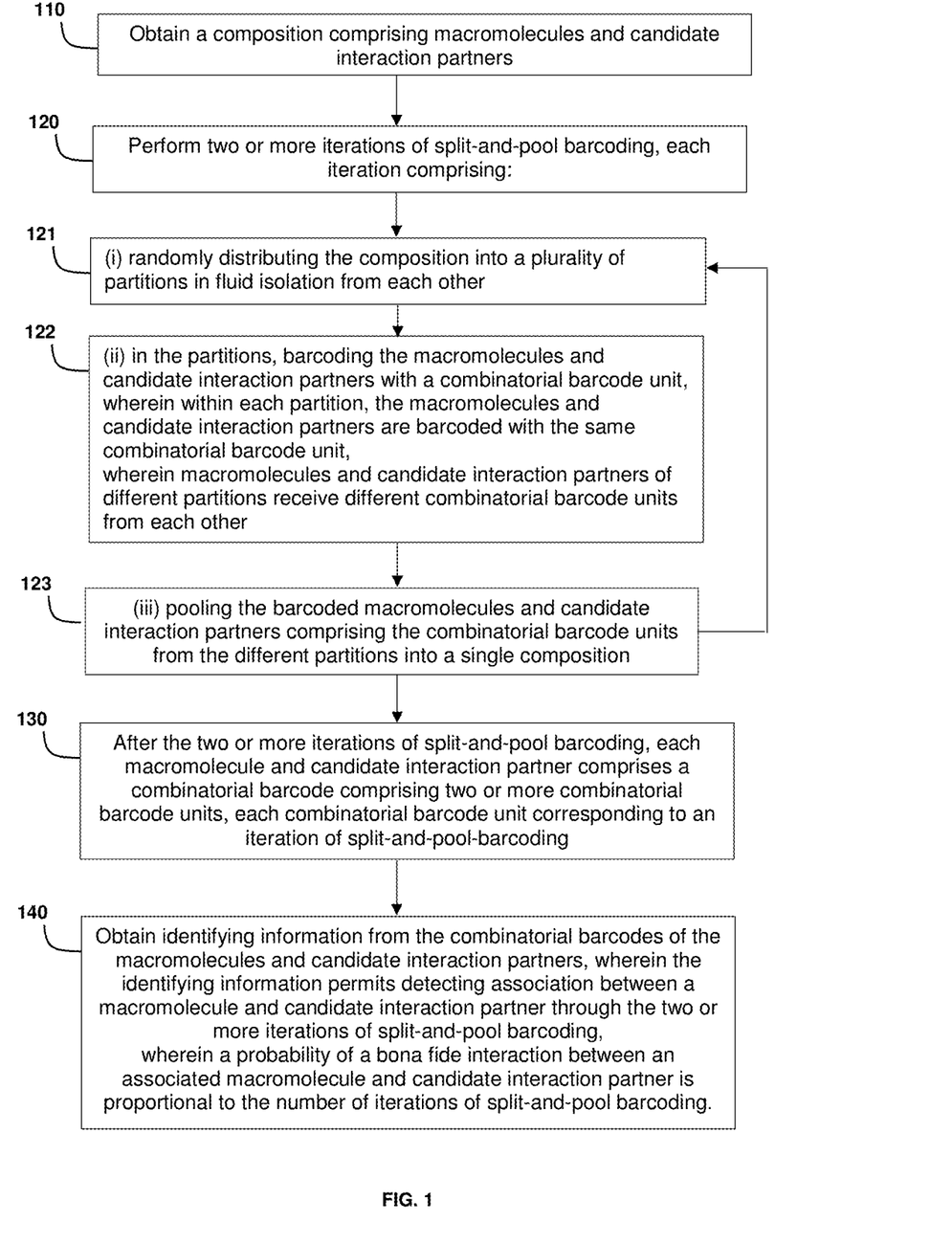
FIG. 1 is a flow diagram illustrating a method of detecting molecular interactions using combinatorial barcoding in accordance with some embodiments herein.

With reference to FIG. 1, a method of detecting an interaction between a macromolecule and an interaction partner of some embodiments is depicted. The detecting method can comprise obtaining a composition comprising macromolecules and candidate interaction partners 110. The detecting method can comprise performing two or more iterations of split-and-pool barcoding 120, example at least 2, 3, 4 5, 6 7, 8, 9, 10, 11, 12, 13, 14, 15, 16, 17, 18, 19, 20, 21, 22, 23, 24, 25, 25, 27, 28, 29, or 30 iterations, including ranges between any two of the listed values, for example, 2-5 iterations, 2-10 iterations, 2-15 iterations, 2-25 iterations, 2-30 iterations, 5-10 iterations, 5-15 iterations, 5-25 iterations, 5-30 iterations, 7-10 iterations, 7-15 iterations, 7-25 iterations, 7-30 iterations, 10-15 iterations, 10-25 iterations or 10-30 iterations, each iteration comprising: (i) randomly distributing the composition into a plurality of partitions in fluid isolation from each other 121; (ii) in the partitions, barcoding the macromolecules and candidate interaction partners with a combinatorial barcode unit, wherein within each partition, the macromolecules and candidate interaction partners are barcoded with the same combinatorial barcode unit, wherein macromolecules and candidate interaction partners of different partitions receive different combinatorial barcode units from each other 122; and (iii) pooling the barcoded macromolecules and candidate interaction partners comprising the combinatorial barcode units from the different partitions into a single composition 123. After the two or more iterations of split-and-pool barcoding (items 121, 122, and 123), each macromolecule and candidate interaction partner comprises a combinatorial barcode comprising two or more combinatorial barcode units, each combinatorial barcode unit corresponding to an iteration of split-and-pool-barcoding 130. Then, the detecting method can comprise obtaining identifying information from the combinatorial barcodes of the macromolecules and candidate interaction partners, wherein the identifying information permits detecting association between a macromolecule and candidate interaction partner through the two or more iterations of split-and-pool barcoding, wherein a probability of a bona fide interaction between an associated macromolecule and candidate interaction partner is proportional to the number of iterations of split-and-pool barcoding 140. In some embodiments, macromolecules are of a library of in vitro translated polypeptides. Each macromolecule can comprise an identifier barcode comprising a polynucleotide comprising a coding sequence of the macromolecule, such as an mRNA encoding the macromolecule.

By combinatorically barcoding each macromolecule and candidate interaction partner, the detecting method can detect molecular interactions such as protein-protein, protein-RNA, and protein-DNA interactions by sorting these molecules over multiple iterations of split-and pool barcoding. For example, after 8 iterations of split-and-pool barcoding, trillions of interactions ($>10^{15}$) can be detected, which is orders of magnitude larger than the number of interactions that can typically be screened by conventional methods. In the detecting method of some embodiments, at least $10^3$, $10^4$, $10^5$, $10^6$, $10^7$, $10^8$, $10^9$, $10^{10}$, $10^{11}$, $10^{12}$, $10^{13}$, $10^{14}$, or $10^{15}$ different interactions are screened.

In the detecting method of some embodiments, macromolecules are of a library of in vitro translated polypeptides. For example, the library can comprise macromolecules that are being screened for interactions with one or more candidate interaction partners. The library may be free of cellular components such as organelles.

In the detecting method of some embodiments, the macromolecules are of a library of in vitro translated polypeptides, and each macromolecule comprises an "identifier barcode" comprising a polynucleotide comprising a coding sequence of the macromolecule such as an mRNA encoding the macromolecule. For example, the macromolecules can be translated in vitro from a polynucleotide encoding the macromolecule, in which a polypeptide tag is fused to the polynucleotide. The polynucleotide can further encode a counterpart polypeptide sequence that is part of the macromolecule, and specifically covalently binds to the polypeptide tag. The counterpart polypeptide sequence can be disposed in an N-terminal region of the macromolecule. As such, the polypeptide tag can co-translationally (or immediately following translation) form a covalent bond with the counterpart polypeptide sequence. For example, a 5' portion of the polynucleotide can encode the counterpart polypeptide sequence so that an N-terminal portion of the macromolecule comprises the counterpart polypeptide sequence. Under these approaches, the macromolecule can be barcoded with an identifier barcode comprising the polynucleotide comprising the coding sequence of the macromolecule. Optionally, the polynucleotide of the identifier barcode may further comprise a random oligonucleotide barcode, for example a random oligonucleotide barcode of at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides, including ranges between any two of the listed values, for example, 3-10, 3-20, 3-30, 3-50, 6-10, 6-20, 6-30, 6-50, 10-20, 10-30, 10-50, 20-30, or 20-50 nucleotides. Examples of suitable covalent polypeptide tag and counterpart polypeptide sequences include, but are not limited to, spilt CnaB proteins (See, e.g., Pröschel et al., PLoS One 12(6):e0179740, which is hereby incorporated by reference in its entirety) such as a Spytag and SpyCatcher; or Isopeptag and pilin-C; or SnoopTag and SnoopCatcher; or DogTag and SnoopTagJr; or SdyTag and SdyCatcher. In some embodiments, the covalent polypeptide tag and counterpart polypeptide sequences comprise a split CnaB protein, or Spytag and SpyCatcher; or Isopeptag and pilin-C; or SnoopTag and SnoopCatcher; or DogTag and SnoopTagJr; or SdyTag and SdyCatcher, or a combination of two or more of the listed items. In some embodiments, the covalent polypeptide tag and counterpart polypeptide sequences comprise a Spytag and SpyCatcher; or Isopeptag and pilin-C; or SnoopTag and SnoopCatcher; or DogTag and SnoopTagJr; or SdyTag and SdyCatcher, or a combination of two or more of the listed items. Additional information on example polypeptide tags and counterpart polypeptides is shown in Table 1. It will be appreciated that the listed pairs specifically form covalent bonds with each other, and thus either member of the listed pairs may serve as a "polypeptide tag" in accordance with detecting methods and kits of some embodiments herein, provided that the other pair member serves as the "counterpart polypeptide sequence." Thus, for example, a Spytag may serve as a "polypeptide tag" while a SpyCatcher serves as a "counterpart polypeptide sequence," or SpyCatcher may serve as a "polypeptide tag" while a SpyTag serves as a "counterpart polypeptide sequence.

TABLE 1

Example polypeptide tags and counterpart polypeptide sequences

| First pair member | Second pair member |
| --- | --- |
| isopeptag (such as TDKDMTIT FTNKKDAE-SEQ ID NO: 1) | pilin-C protein |
| SpyTag (such as AHIVMVDAYKP TK-SEQ ID NO: 2) | SpyCatcher protein |
| SnoopTag (such as KLGDIEFIK VNK-SEQ ID NO: 3) | SnoopCatcher protein |
| DogTag (such as DIPATYEFTDG KHYITNEPIPPK-SEQ ID NO: 4) | SnoopTagJr |
| SdyTag (such as DPIVMIDNDKPI T-SEQ ID NO: 5) | SdyCatcher |

Figures 4A, 4B:
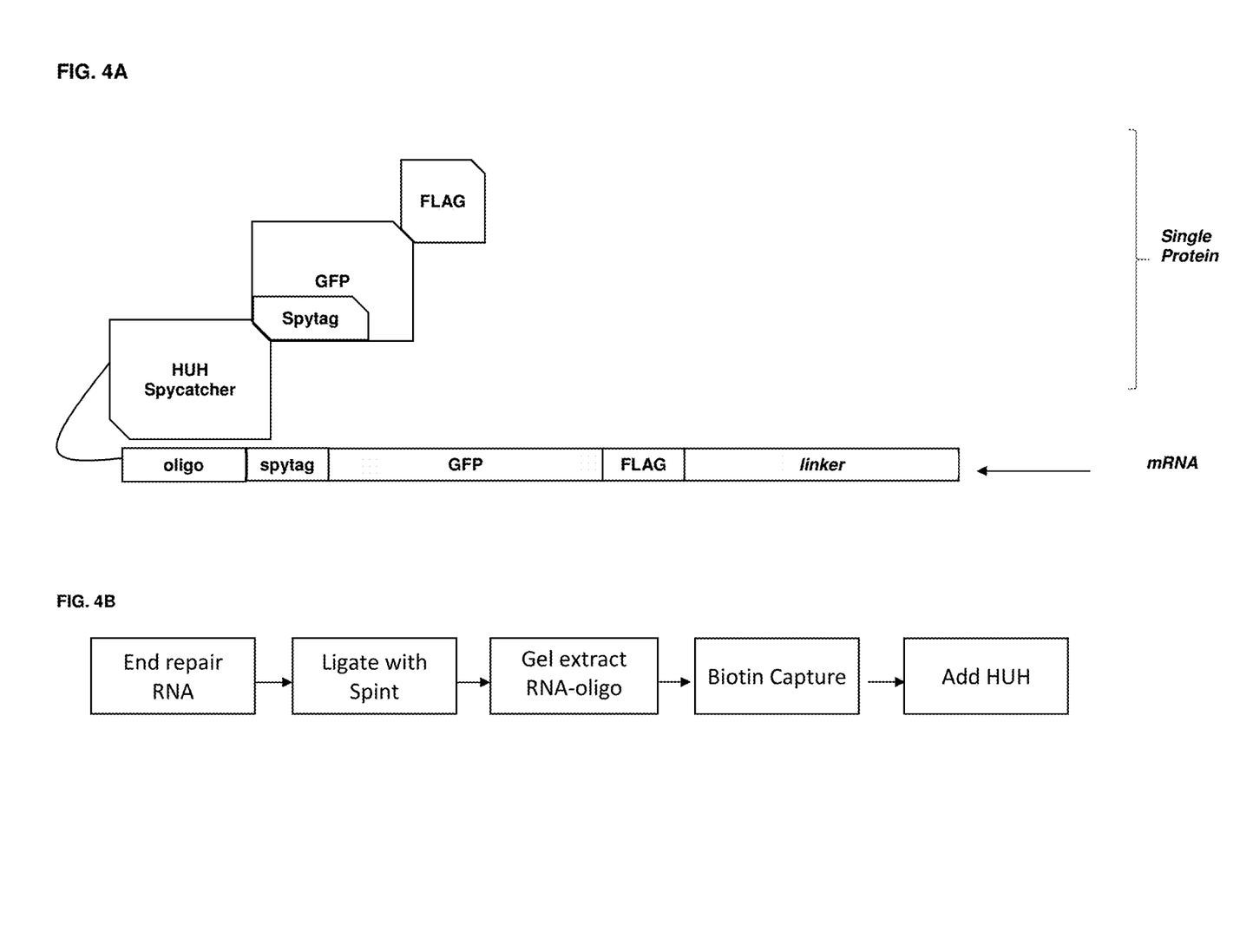
FIGS. 4A-C are a series of schematic diagrams and graphs showing construction and purification of macromolecules comprising identifier barcodes in accordance with some embodiments.

A schematic diagram of a macromolecule comprising an identifier barcode in accordance with some embodiments is shown in FIG. 4A. An mRNA molecule can be covalently bound to a macromolecule (or candidate interaction partner) using a polypeptide tag and counterpart polypeptide sequence that specifically form a covalent bond, such as a SpyTag-SpyCatcher mediated approach. A ribosome system can be used to express the macromolecule (or candidate interaction partner), which is fused to a polypeptide tag such as SpyTag. The mRNA can be ligated to an oligonucleotide that is coupled to a spy-catcher protein via a protein-oligonucleotide conjugation, such a HUH protein, SMCC linkage, or RepB replicase. The protein/mRNA linkage can be performed any number of reaction environments, for example, bacterial transcription/translation systems. Using this system, nascent translation of the mRNA produces a protein that, via a polypeptide tag and counterpart polypeptide sequence (such as SpyCatcher-SpyTag conjugation, or other systems) is covalently linked to its cognate mRNA. To facilitate fidelity of co-translational or immediately post-translational (nascent) RNA/nascent protein conjugation, the detecting method of some embodiments may comprise additional stalling sequences and/or translation in oil-in-water emulsions. As described in Example 1, a SpyCatcher-SpyTag linkage was characterized by performing immunoprecipitation of nanobody proteins containing FLAG-tag in a mixed system containing nascent proteins with mRNAs containing FLAG and no tag at all ("GS") coupled to a cognate SpyCatcher. QPCR for FLAG-specific sequence showed high levels of enrichment (>90%) of FLAG sequence (RNA) after FLAG immunoprecipitation (protein). In the absence of ligated HUH-SpyCatcher, this was not the case, indicating that the polypeptide tag and counterpart polypeptide sequence maintained a covalent bond between the nanobody and the mRNA (See FIG. 4C).

It is noted that identifier barcodes comprising coding sequence of the macromolecule can be sequenced to identify the macromolecule as well. Thus, in a library of macromolecules, sequencing the identifier barcode and combinatorial barcode can not only identify a likely intermolecular interaction, but can also detect the structure of the macromolecule in a particular interaction. Accordingly, in the detecting method of some embodiments, obtaining sequence information from the combinatorial barcodes of the macromolecules and candidate interaction partners further comprises obtaining sequence information of the coding sequence of the macromolecule. In the detecting method of some embodiments, the candidate interaction partner also comprises an identifier barcode comprising a nucleic acid sequence encoding the candidate interaction partner.

In some embodiments, the detecting method further comprises fusing polypeptide tags to a library of polynucleotides encoding a library of macromolecules. As used herein "fusing" (and variations of this root term) has its ordinary and customary meaning as would be understood by one of ordinary skill in the art in view of this disclosure. It refers to a forming covalent linkage between two molecules. Thus, a polynucleotide that is "fused" to a polypeptide tag is covalently bound to the polypeptide tag. The polypeptide tags can be fused to a library of polynucleotides by any of a number of forms of covalent attachment. For example, the polypeptide tag may further comprise a HUH protein, SMCC linkage, or RepB replicase which forms a covalent bond with a polynucleotide of the library. It will be appreciated that "HUH proteins," "SMCC linkages," and "RepB replicase" suitable for forming fusing to polynucleotides or oligonucleotides as described herein encompass full-length proteins, as well as covalent-bond-with-polynucleotide-forming fragments thereof. For example, the polynucleotide can be synthesized with a primary amine or thiol group, and an amine- or sulfhydryl-reactive crosslinker can covalently bind the polynucleotide to the polypeptide tag. In the detecting method of some embodiments, the polynucleotide can encode a counterpart polypeptide sequence that is part of the macromolecule, and specifically covalently binds to the polypeptide tag. Accordingly, when the coding sequence of the polynucleotide is translated, the macromolecule comprising the counterpart polypeptide sequence covalently binds to the polynucleotide comprising the coding sequence of the macromolecule.

The detecting method of some embodiments comprises fusing the covalent polypeptide tag to the polynucleotide as described herein, translating the polynucleotide in vitro (thus producing the macromolecule comprising the counterpart polypeptide sequence disposed at the N-terminal portion), and covalently binding the polypeptide tag to the counterpart polypeptide sequence (thus making the macromolecule comprising the identifier barcode).

In the detecting method of some embodiments, each combinatorial barcode unit comprises a handle (which may also be referred to as a "linker") and a complement of the handle. The complement of the handle and the handle can each be disposed on different terminal portions of their respective molecule, and can permit the addition of additional combinatorial barcode units to a growing combinatorial barcode through the annealing and ligation of a handle to its complement. In the detecting method of some embodiments, the identifier barcode comprises a complement of a handle. The complement of the handle on the identifier barcode can anneal to the handle of a combinatorial barcode unit. The combinatorial barcode unit can be ligated to the identifier barcode via the annealed handle and complement thereof, and can further comprise a complement of the handle for adding an additional combinatorial barcode unit in the next round of split-and-pool barcoding. Accordingly, in the detecting methods of some embodiments, the macromolecules, candidate interaction partners, and combinatorial barcode units are incubated with ligase. In the detecting methods of some embodiments, the partitions comprise ligase, in addition to the macromolecules, candidate interaction partners, and combinatorial barcode units. In the detecting method of some embodiments, the method comprises adding a ligase to the macromolecules and candidate interaction partners. For example, combinatorial barcode units and ligase can be added separately or together to the macromolecules and candidate interaction partners, or the partitions can comprise combinatorial barcode units and/or ligase and the macromolecules and candidate interaction partners can be added to the partitions. In some embodiments, different handles and complements are used in different iterations of split-and-pool barcoding to avoid polymerization of combinatorial barcode units.

In the detecting method of some embodiments, the identifier barcode further comprises a random oligonucleotide barcode, for example a random oligonucleotide barcode of at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides, including ranges between any two of the listed values, for example, 3-10, 3-20, 3-30, 3-50, 6-10, 6-20, 6-30, 6-50, 10-20, 10-30, 10-50, 20-30, or 20-50 nucleotides. In the detecting method of some embodiments, the identifier barcode further comprises a random oligonucleotide barcode of at least 5 nucleotides.

The combinatorial barcode units of methods of detecting as described herein can comprise oligonucleotides. By way of example, different combinatorial barcode units can be differentiated by different nucleic acid sequences, and/or by different combinations and/or arrangements of detectable moieties such as fluorophores, nanoparticles, and/or quantum dots. As such, a combinatorial barcode can comprise a combination of combinatorial barcode unit sequences that provide identifying information, and/or a combination of detectable moieties that provide identifying information. Examples of detectable moieties include, but are not limited to, xanthene dyes (e.g., fluorescein) and rhodamine dyes, such as fluorescein isothiocyanate (FITC), 2-[ethylamino)-3-(ethylimino)-2-7-dimethyl-3H-xanthen-9-yl]benzoic acid ethyl ester monohydrochloride (R6G) (emits a response radiation in the wavelength that ranges from about 500 to 560 nm), 1,1,3,3,3',3'-Hexamethylindodicarbocyanine iodide (HIDC) (emits a response radiation in the wavelength that ranged from about 600 to 660 nm), 6-carboxyfluorescein (commonly known by the abbreviations FAM and F), 6-carboxy-2',4',7',4,7-hexachlorofluorescein (HEX), 6-carboxy-4',5'-dichloro-2',7'-dimethoxyfluorescein (JOE or J), N,N,N',N'-tetramethyl-6-carboxyrhodamine (TAMRA or T), 6-carboxy-X-rhodamine (ROX or R), 5-carboxyrhodamine-6G (R6G5 or G5), 6-carboxyrhodamine-6G (R6G6 or G6), and rhodamine 110; cyanine dyes, e.g. Cy3, Cy5 and Cy7 dyes; coumarins, e.g., umbelliferone; benzimide dyes, e.g. Hoechst 33258; phenanthridine dyes, e.g. Texas Red; ethidium dyes; acridine dyes; carbazole dyes; phenoxazine dyes; porphyrin dyes; polymethine dyes, e.g. cyanine dyes such as Cy3 (emits a response radiation in the wavelength that ranges from about 540 to 580 nm), Cy5 (emits a response radiation in the wavelength that ranges from about 640 to 680 nm); BODIPY dyes and quinoline dyes. Specific fluorophores of interest include: Pyrene, Coumarin, Diethylaminocoumarin, FAM, Fluorescein Chlorotriazinyl, Fluorescein, R110, Eosin, JOE, R6G, HIDC, Tetramethylrhodamine, TAMRA, Lissamine, ROX, Napthofluorescein, Texas Red, Napthofluorescein, Cy3, and Cy5, and the like), radioisotopes (e.g. $^{18}$F, $^{32}$P, $^{33}$P, $^{45}$Ti, $^{47}$Sc, $^{52}$Fe, $^{59}$Fe, $^{62}$Cu, $^{64}$Cu, $^{67}$Cu, $^{67}$Ga, $^{68}$Ga, $^{75}$Sc, $^{77}$As, $^{86}$Y, $^{90}$Y, $^{89}$Sr, $^{89}$Zr, $^{94}$Tc, $^{99}$Mo, $^{105}$Pd, $^{105}$Rh, $^{111}$Ag, $^{111}$In, $^{124}$I, $^{125}$I, $^{131}$I, $^{142}$Pr, $^{143}$Pr, $^{149}$Pm, $^{153}$Sm, $^{161}$Tb, $^{166}$Dy, $^{166}$Ho, $^{169}$Er, $^{175}$Lu, $^{177}$Lu, $^{186}$Re, $^{188}$Re, $^{189}$Re, $^{194}$Ir, $^{198}$Au, $^{199}$Au, $^{211}$At, $^{211}$Pb, $^{212}$Bi, $^{212}$Pb, $^{213}$Bi, $^{223}$Ra, nanoparticles (e.g. comprising gold, platinum, transition metal oxide, and/or any of the radioisotopes described herein), or a combination of two or more of any of the listed items. In the detecting method of some embodiments, the combinatorial barcode units comprise oligonucleotides, and different oligonucleotide sequences differentiate different combinatorial barcode units from each other. In the detecting method of some embodiments, the combinatorial barcode units comprise detectable moieties such as fluorophores, wherein different detectable moieties differentiate different combinatorial barcode units from each other. The detectable moieties can be bound to oligonucleotides. For example, a combinatorial barcode in accordance with some embodiments herein comprises a polyfluorophore, in which the sequence and types of fluorophores provides the barcoding information.

In the detecting method of some embodiments, obtaining identifying information from the combinatorial barcodes of the macromolecules and candidate interaction partners comprises sequencing the combinatorial barcodes. Any next-generation/high-throughput sequencing technology currently known and/or in development can be used to perform the sequencing disclosed herein. Non-limiting examples include massively parallel signature sequencing (MPSS), polony sequencing, single-molecule real-time sequencing (Pacific Biosciences) Illumina (Solexa) sequencing, Roche 454 sequencing, ion torrent semiconductor sequencing, sequencing by ligation (SOLiD) sequencing, pyrosequencing, shotgun sequencing, nanopore sequencing, chain termination (Sanger) sequencing, DNA nanoball sequencing, heliscope single molecule sequencing, and single molecule real time (SMRT) sequencing. In the detecting methods of some embodiments, obtaining identifying information from the combinatorial barcodes of the macromolecules and candidate interaction partners comprises detecting detectable moieties of the barcodes.

In the detecting methods of some embodiments, the macromolecules are selected from the group consisting of proteins, RNA binding proteins, antigen binding proteins, antibodies or fragments thereof, scFvs, nanobodies, and aptamers. Optionally, the macromolecules comprise an identifier barcode as described herein. For a macromolecule comprising a polypeptide, the identifier barcode can comprise coding sequence of the macromolecule.

In the detecting methods of some embodiments, the candidate interaction partners are selected from the group consisting of: proteins, peptides, RNAs, DNAs, and small molecules. Optionally, the macromolecules are proteins or peptides and comprise an identifier barcode as described herein. The identifier barcode can comprise coding sequence of the candidate interaction partner, for example if a candidate interaction partner comprises a polypeptide. In some embodiments, the candidate interaction partners are molecules of the same type (e.g., all small molecules or all peptides). In some embodiments, the candidate interaction partners comprise a mixture of different types of molecules (for example, peptides and small molecules to identify small molecules that interfere with peptide-macromolecule interactions.

In the detecting method of some embodiments, the composition comprises a library of macromolecules, and/or a library of candidate interaction partners. In the detecting method of some embodiments, the composition comprises at least $10^3$ different macromolecules and at least $10^3$ different candidate interaction partners. In the detecting method of some embodiments, the composition comprises at least $10^3$ different macromolecules and at least $10^6$ different candidate interaction partners. In the detecting method of some embodiments, the composition comprises at least $10^6$ different macromolecules and at least $10^3$ different candidate interaction partners. In the detecting method of some embodiments, the composition comprises at least $10^6$ different macromolecules and at least $10^6$ different candidate interaction partners.

It is contemplated that detecting methods of some embodiments can not only identify intermolecular interactions, but can also identify molecules that inhibit intermolecular interactions. If a first macromolecule and a first candidate interaction partner are associated through the two or more iterations of split-and-pool barcoding, and if a second macromolecule or candidate interaction partner associates with the macromolecule and a candidate interaction partner, but there is no trimeric association between (i) the first macromolecule, (ii) the first candidate interaction partner, and (iii) the second macromolecule or candidate interaction partner, it can be inferred that the second macromolecule or candidate interaction partner may inhibit the interaction between the first macromolecule and the first candidate interaction partner. For example, if "macromolecule A" and "candidate interaction partner B" are determined, through combinatorial barcoding, to be associated in 15 out of 15 iterations of combinatorial barcoding, and "macromolecule A" and "candidate interaction partner C" are determined, through combinatorial barcoding, to be associated in 15 out of 15 iterations of combinatorial barcoding, but there is no association between all three of "macromolecule A," "candidate interaction partner B," and "macromolecule A" and "candidate interaction partner C," in the same partition through the 15 iterations of combinatorial barcoding, it can be inferred that "candidate interaction partner C" is likely to interfere with the association of "macromolecule A" and "candidate interaction partner B." Accordingly, in the detecting method of some embodiments, a macromolecule associates with a first candidate interaction partner through the split-and-pool barcoding, and a second candidate interaction partner associates with the macromolecule through the split-and-pool barcoding, but all three of the macromolecule, the first candidate interaction partner, and the second candidate interaction partner do not associate through the split-and-pool barcoding. This can indicate that the second candidate interaction partner has a probability of interfering with the association between the macromolecule and the first interaction partner. For example, the macromolecule can comprise an antibody or fragment thereof, and the first and second candidate interaction partner may each occupy an overlapping space in the binding pocket of the antibody.

In the detecting method of some embodiments, a first macromolecule associates with a candidate interaction partner through the split-and-pool barcoding, and a second macromolecule associates with the candidate interaction partner through the split-and-pool barcoding, but all three of the first macromolecule, the second macromolecule, and the candidate interaction partner do not associate through the split-and-pool barcoding. This can indicate that the second macromolecule has a probability of interfering with the association between the macromolecule and the first interaction partner. For example, the first macromolecule and the second macromolecule can each comprise an antibody or fragment thereof, and may compete with each other for binding to the same candidate interaction partner.

In the detecting method of some embodiments, at least 2, 3, 4, 5, 6, 7, 8, 9, 10, 11, 12 13, 14, 15, 16, 17, 18, 19, 20, 21, 22, 23, 24, 25, 26, 27, 28, 29, or 30 iterations of split-and-pool barcoding are performed, including ranges between any two of the listed values, for example, 2-5 iterations, 2-7 iterations, 2-10 iterations, 2-15 iterations, 2-20 iterations, 2-30, 3-5 iterations, 3-7 iterations, 3-10 iterations, 3-15 iterations, 3-20 iterations, 3-30, 5-7 iterations, 5-10 iterations, 5-15 iterations, 5-20 iterations, 5-30, 7-10 iterations, 7-15 iterations, 7-20 iterations, 7-30 iterations, 10-15 iterations, 10-20 iterations, 10-30 iterations, 15-20 iterations, or 15-30 iterations.

Kits

In some embodiments, kits are described. The kit can comprise a vector comprising an insertion site and counterpart polypeptide coding sequence. The insertion site is arranged to place a protein coding sequence in frame with the counterpart polypeptide coding sequence without any intervening stop codon, upon the insertion of the protein coding sequence in the insertion site. The kit can comprise a covalent polypeptide tag, in which the covalent polypeptide tag and the counterpart polypeptide sequence are configured to specifically covalently bind to each other. For example, the covalent polypeptide tag can be configured to be fused to an mRNA comprising the protein coding sequence. By way of example, the covalent polypeptide tag may comprise a protein that binds to a polynucleotide, such as a protein selected from the group consisting of a HUH protein, a SMCC linkage, and a RepB replicase, or a combination of two or more of the listed items. The kit can comprise at least two different combinatorial barcode units as described herein, for example, at least 2, 3, 4, 5, 6, 7, 8, 9, 10, 11, 12, 13, 14, 15, 16, 17, 18, 19, 20, 30, 40, 50, 60, 70, 80, 90, 100, 150, 200, 250, 300, 350, 400, 450, or 500 different combinatorial barcode units, including ranges between two or more of any of the listed values, for example 2-50, 2-100, 2-500, 10-50, 10-100, 10-500, 50-100, 50-500, or 100-500 different combinatorial barcode units.

As used herein "vector" has its customary and ordinary meaning as would be understood by one of ordinary skill in the art in view of this disclosure. It refers to a construct configured to contain a nucleic acid (such as a nucleic acid encoding a protein such as a macromolecule as described herein), and provide that nucleic acid to a host cell. Examples of suitable vectors for kits, and compositions of some embodiments include, but are not limited to a plasmids and viral vectors, for example, an adenoviral vector or adeno associated viral vector. Vectors can include, for example, plasmids such as pSVL and pKSV-10 available from Pharmacia, pBPV-1/pML2d (International Biotechnologies, Inc.), and pCDNA and pTDT1 (ATCC, #31255); viral vectors such based on vaccinia virus, poliovirus, adenovirus, herpes simplex virus, a lentivirus; vectors derived from retroviruses such as Rous Sarcoma Virus, Harvey Sarcoma Virus, avian leukosis virus, human immunodeficiency virus, myeloproliferative sarcoma virus, and mammary tumor virus); adeno-associated virus vectors, and the like. Additional examples of suitable eukaryotic vectors include bovine papilloma virus-based vectors, Epstein-Barr virus-based vectors, SV40, 2-micron circle, pcDNA3.1, pcDNA3.1/GS, pYES2/GS, pMT, pIND, pIND(Sp1), pVgRXR (Invitrogen), and the like. Derivatives and variants of any of the listed vectors are also contemplated in some embodiments.

Generation of a vector comprising the nucleic acid encoding the protein (such as a macromolecule) can be accomplished using any suitable genetic engineering techniques well known in the art, including, without limitation, the techniques such as restriction endonuclease digestion, ligation, transformation, plasmid purification, and DNA sequencing, for example as described in Green and Sambrook (Molecular Cloning: A Laboratory Manual. 4th Edition. Cold Spring Harbor Laboratory Press, N.Y. (2012)), which is incorporated by reference in its entirety herein.

In some embodiments, any vector as described herein comprises an insertion site. By way of example, the insertion site may comprise one or more restriction endonuclease sites, a multiple cloning site (MCS), or a GATEWAY destination site. The insertion site can be disposed for the insertion of a nucleic acid encoding a query protein in a desired location on the vector. For example, the vector can comprise a promoter, and the insertion site may be positioned 3' to the promoter, for example within 10 bp, 20, 30, 40, 50, 100, 150, 200, 250, 300, 400, 500, 600, 700, 800, 900, 1000, 1100, 1200, 1500, or 2000 bp 3' to the promoter. Suitable promoters can be selected for the desired expression environment. For example, the promoter may comprise a robust promoter such as the cytomegalovirus (CMV) promoter.

In the kit of some embodiments, the different combinatorial barcode units comprise oligonucleotides having different sequences, and/or the different combinatorial barcode units comprise different detectable moieties as described herein, for example, fluorophores.

Additional Embodiments

In addition to the items noted above, the following options are set forth:

1. A method of detecting an interaction between a macromolecule and an interaction partner, the method comprising:
   obtaining a composition comprising macromolecules and candidate interaction partners;
   performing two or more iterations of split-and-pool barcoding, each iteration comprising:
      (i) randomly distributing the composition into a plurality of partitions in fluid isolation from each other;
      (ii) in the partitions, barcoding the macromolecules and candidate interaction partners with a combinatorial barcode unit,
         wherein within each partition, the macromolecules and candidate interaction partners are barcoded with the same combinatorial barcode unit,
         wherein macromolecules and candidate interaction partners of different partitions receive different combinatorial barcode units from each other; and
      (iii) pooling the barcoded macromolecules and candidate interaction partners comprising the combinatorial barcode units from the different partitions into a single composition,
   wherein, after the two or more iterations of split-and-pool barcoding, each macromolecule and candidate interaction partner comprises a combinatorial barcode comprising two or more combinatorial barcode units, each combinatorial barcode unit corresponding to an iteration of split-and-pool-barcoding; and
   obtaining identifying information from the combinatorial barcodes of the macromolecules and candidate interaction partners, wherein the identifying information permits detecting association between a macromolecule and candidate interaction partner through the two or more iterations of split-and-pool barcoding,
   wherein a probability of a bona fide interaction between an associated macromolecule and candidate interaction partner is proportional to the number of iterations of split-and-pool barcoding.

2. The method of option 1, wherein each macromolecule is a protein, and wherein each macromolecule comprises an identifier barcode comprising an polynucleotide comprising a coding sequence of the macromolecule.

3. The method of option 2, wherein the identifier barcode further comprises a covalent polypeptide tag fused to the polynucleotide, and wherein the protein further comprises a counterpart polypeptide sequence covalently bound to the polynucleotide.

4. The method of option 3, wherein the counterpart polypeptide sequence is disposed at an N-terminal region of the protein.

5. The method of any one of options 2-4, further comprising
fusing the covalent polypeptide tag to the polynucleotide;
translating the polynucleotide in vitro, thereby producing the macromolecule comprising the counterpart polypeptide sequence disposed at an N-terminal portion of the macromolecule; and
covalently binding the polypeptide tag to the counterpart polypeptide sequence, thereby making the macromolecule comprising the identifier barcode 6. The method of any one of options 3-5, wherein the covalent polypeptide tag and counterpart polypeptide sequence comprise a split CnaB protein; or a Spytag and SpyCatcher; or Isopeptag and pilin-C; or SnoopTag and SnoopCatcher; or DogTag and SnoopTagJr; SdyTag and SdyCatcher.

7. The method of any one of options 3-6, wherein the covalent polypeptide tag is fused to the polynucleotide via a HUH protein, SMCC linkage, or RepB replicase.

8. The method of any one of options 2-7, wherein the identifier barcode further comprises a random oligonucleotide barcode or at least 5 nucleotides.

9. The method of any one of options 2-8, wherein the identifier barcode further comprises a terminal single-stranded handle sequence, and wherein each combinatorial barcode unit comprises a terminal single-stranded complementary to the terminal handle sequence, wherein said barcoding comprises:
permitting the terminal single-stranded handle sequences to anneal to the terminal single-stranded complements; and
ligating the terminal handle sequences to the terminal complements.

10. The method of any one of options 1-9, wherein the combinatorial barcode units comprise oligonucleotides, wherein different oligonucleotide sequences differentiate different combinatorial barcode units from each other; or
wherein the combinatorial barcode units comprise detectable moieties, wherein different detectable moieties differentiate different combinatorial barcode units from each other.

11. The method of any one of options 2-10, wherein obtaining sequence information from the combinatorial barcodes of the macromolecules and candidate interaction partners further comprises obtaining sequence information of the coding sequence of the macromolecule.

12. The method of any one of options 1-11, wherein the macromolecules are of a library of in vitro translated polypeptides.

13. The method of any one of options 1-12, wherein the macromolecules are selected from the group consisting of proteins, RNA binding proteins, antigen binding proteins, antibodies or fragments thereof, scFvs, nanobodies, and aptamers, or a combination of two or more of any of the listed items.

14. The method of any one of options 1-13, wherein the candidate interaction partners are selected from the group consisting of: proteins, peptides, RNAs, DNAs, and small molecules, or a combination of two or more of any of the listed items.

15. The method of any one of options 1-14, wherein the composition comprises at least $10^3$, different macromolecules and at least $10^3$ different candidate interaction partners.

16. The method of any one of options 1-15, wherein the composition comprises at least $10^6$, different macromolecules and at least $10^6$ different candidate interaction partners.

17. The method of any one of options 1-16, wherein a macromolecule associates with a first candidate interaction partner through the split-and-pool barcoding, and wherein a second candidate interaction partner associates with the macromolecule through the split-and-pool barcoding, but all three of the macromolecule, the first candidate interaction partner, and the second candidate interaction partner do not associate through the split-and-pool barcoding,
thereby indicating that the second candidate interaction partner has a probability of interfering with the association between the macromolecule and the first interaction partner.

18. The method of any one of options 1-16, wherein a first macromolecule associates with a candidate interaction partner through the split-and-pool barcoding, and wherein a second macromolecule associates with the candidate interaction partner through the split-and-pool barcoding, but all three of the first macromolecule, the second macromolecule, and the candidate interaction partner do not associate through the split-and-pool barcoding,
thereby indicating that the second macromolecule has a probability of interfering with the association between the macromolecule and the first interaction partner.

19. The method of any one of options 1-18, comprising at least 3 iterations of split-and-pool barcoding.

20. A kit comprising:
a vector comprising an insertion site and counterpart polypeptide coding sequence, wherein the insertion site is arranged to place a protein coding sequence in frame with the counterpart polypeptide coding sequence without any intervening stop codon, upon the insertion of the protein coding sequence in the insertion site;
a covalent polypeptide tag, wherein the covalent polypeptide tag and the counterpart polypeptide sequence are configured to specifically covalently bind to each other; and
at least two different combinatorial barcode units.

21. The kit of option 20, wherein the covalent polypeptide tag further comprises a protein that binds to a polynucleotide.

22. The kit of option 21, wherein the protein that binds to a polynucleotide is selected from the group consisting of a HUH protein, a SMCC linkage, and a RepB replicase, or a combination of two or more of the listed items.

23. The kit of any one of options 20-22, wherein the different combinatorial barcode units comprise oligonucleotides having different sequences, and/or
wherein the different combinatorial barcode units comprise different fluorophores.

Example 1

Figure 4C:
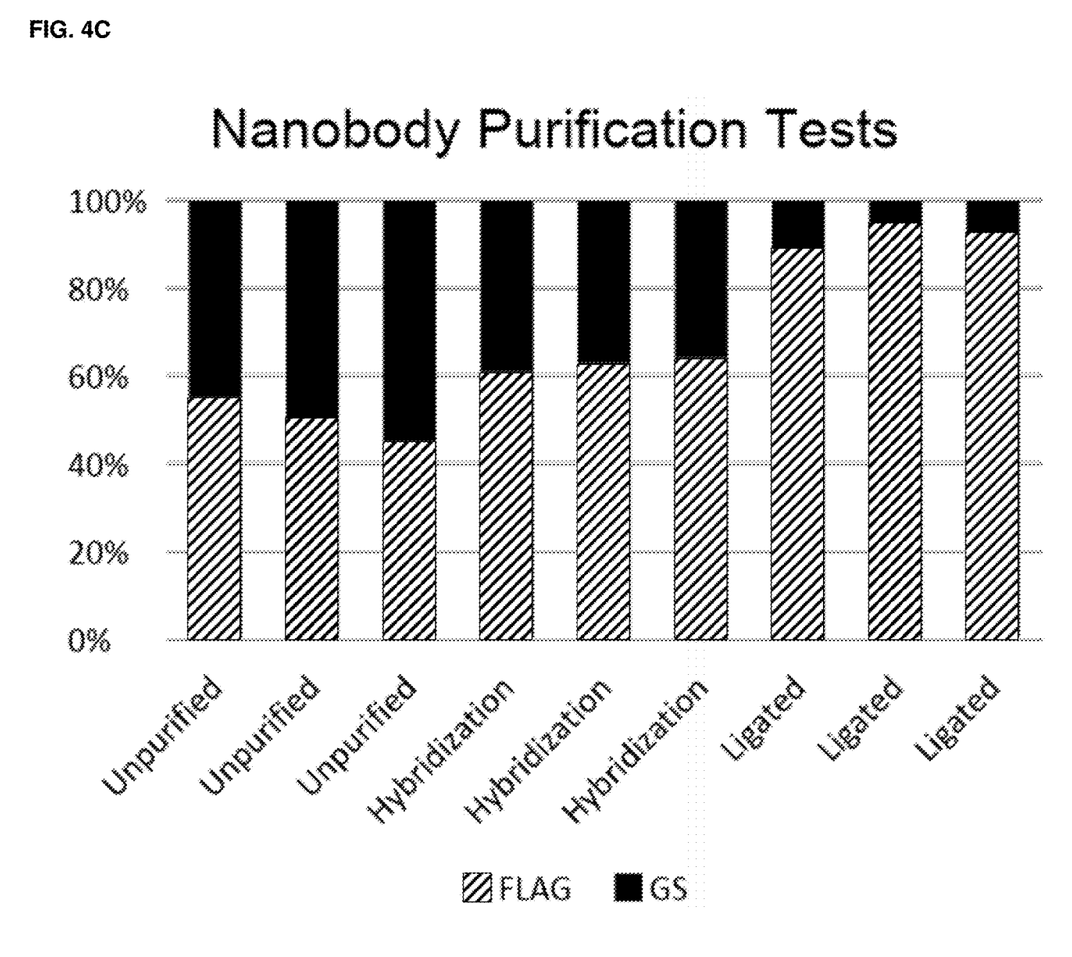

An mRNA molecule is covalently tethered to a protein (an example of a macromolecule) using a SpyTag mediated approach. A ribosome system is used to express the protein of interest, which is fused to a SpyTag. The mRNA is ligated to an oligonucleotide that is coupled to a spy-catcher protein via conjugation to a HUH protein. Using this system, nascent translation of the mRNA produces a protein that (via spycatcher-spytag conjugation) is covalently linked to its cognate mRNA. Characterization of this linkage was performed by immunoprecipitation of proteins containing FLAG-tag in a mixed system containing nascent proteins with mRNAs containing FLAG and no tag at all ("GS") coupled to a cognate Spycatcher. QPCR for FLAG-specific sequence showed high levels of enrichment (>90%) of FLAG sequence (RNA) after FLAG immunoprecipitation (protein) (FIG. 4C). In the absence of ligated HUH-spy-catcher, this was not the case. The protein/mRNA linkage can be performed in solution using (but not limited to) bacterial transcription/translation systems. Thus, in accordance with some embodiments herein, proteins such as macromolecules (e.g., nanobodies) can be barcoded with identifier barcodes, which remain bound to the macromolecule.

Example 2

A library of 1000 different nanobodies are each bound to TCO-PEG12-NHS via NHS chemistry (in which the NHS ester reacts with a primary amine of the nanobody). The TCO-PEG12-bound nanobodies are each labeled with methyltetrazine-PEG4 bound to a random 8 mer oligonucleotide barcode further comprising a 3' handle, thus producing a library of nanobodies covalently bound to the 8 mer oligonucleotide barcode (which further comprises the 3' handle).

The nanobodies are combined with a library of epitope peptides, in which each peptide is covalently bound to a random 8 mer oligonucleotide barcode further comprising the 5' handle, thus forming a composition. The composition is incubated for 30 minutes at 37° C. The composition is then subjected to seven iterations of split-and-pool barcoding as follows: The composition is partitioned among 96 wells in a 96-well plate. A different 8mer combinatorial barcode unit having a 5' portion that further comprises a complement of the 3' handle is added to each partition (so that all of the nanobodies and epitope peptides in a given partition receive the same 8 mer combinatorial barcode unit, but those of different partitions receive a different 8 mer sequence in their combinatorial barcode unit). The 8 mer combinatorial barcode units are ligated to the 3' handles of the nanobodies and epitope peptides of each partition, thus barcoding the nanobodies and epitope peptides of the same partition with the same 8 mer combinatorial barcode unit, while different partitions are barcoded with different 8 mer combinatorial barcode units. The contents of the partitions are then pooled back into a composition. Six additional iterations of split-and-pool barcoding are then performed, thus performing seven iterations of split-and-pool barcoding, so that each nanobody and epitope peptide comprises a combinatorial barcode. The combinatorial barcodes associated with each nanobody and epitope are sequenced via Illumina (Solexa) sequencing. Nanobodies and peptides comprising the same combinatorial barcode, or substantially similar combinatorial barcodes (for which there is than a 1% probability that the similarities in combinatorial barcodes is attributable to random association through the multiple iterations of split-and-pool barcoding) are identified. Interactions between these nanobodies and epitopes are thus detected.

Example 3

A library of 5000 different nanobodies is produced from 5000 different mRNAs, each comprising a SpyTag polypeptide and a random 8 mer oligonucleotide barcode and a 3' handle, and each encoding a SpyCatcher polypeptide sequence in an N-terminal portion of the nanobody. The SpyTags co-translationally bind to the SpyCatcher polypeptide sequence, so that each nanobody is covalently bound (via the SpyTag-SpyCatcher linkage) to the mRNA that encoded it, which further comprises a random 8 mer barcode and a 3' handle.

The nanobodies are combined with a library of epitope peptides, in which each peptide is covalently bound to a random 8 mer oligonucleotide barcode further comprising the 5' handle, thus forming a composition. The composition is incubated for 30 minutes at 37° C. The composition is then subjected to eight iterations of split-and-pool barcoding as follows: The composition is partitioned among 96 wells in a 96-well plate. A different 8 mer combinatorial barcode unit having a 5' portion that further comprises a complement of the 3' handle is added to each partition (so that all of the nanobodies and epitope peptides in a given partition receive the same 8 mer combinatorial barcode unit, but those of different partitions receive a different 8 mer sequence in their combinatorial barcode unit). The 8 mer combinatorial barcode units are ligated to the 3' handles of the nanobodies and epitope peptides of each partition, thus barcoding the nanobodies and epitope peptides of the same partition with the same 8 mer combinatorial barcode unit, while different partitions are barcoded with different 8 mer combinatorial barcode units. The contents of the partitions are then pooled back into a composition. Seven additional iterations of split-and-pool barcoding are then performed, thus performing eight iterations of split-and-pool barcoding, so that each nanobody and epitope peptide comprises a combinatorial barcode.

The combinatorial barcodes associated with each nanobody and epitope are sequenced via Illumina (Solexa) sequencing. The nanobody sequences are identified along with their associated combinatorial barcodes. Nanobodies and peptides comprising the same combinatorial barcode, or substantially similar combinatorial barcodes (for which there is than a 1% probability that the similarities in combinatorial barcodes is attributable to random association through the multiple iterations of split-and-pool barcoding) are identified. Interactions between these nanobodies and epitopes are thus detected.

REFERENCES

Each of the following references is incorporated by reference in its entirety herein.
1. C. Keryer-Bibens, C. Barreau, H. B. Osborne, Tethering of proteins to RNAs by bacteriophage proteins. *Biol. Cell* (2008), doi:10.1042/BC20070067.
2. D. Lipovsek, A. Plückthun, In-vitro protein evolution by ribosome display and mRNA display. *J. Immunol. Methods* (2004), doi:10.1016/j.jim.2004.04.008.
3. P. A. Barendt, D. T. W. Ng, C. N. McQuade, C. A. Sarkar, Streamlined protocol for mRNA display. *ACS Comb. Sci.* (2013), doi:10.1021/co300135r.
4. T. T. Takahashi, R. J. Austin, R. W. Roberts, mRNA display: Ligand discovery, interaction analysis and beyond. *Trends Biochem. Sci.* (2003), doi:10.1016/S0968-0004(03)00036-7.
5. D. S. Wilson, A. D. Keefe, J. W. Szostak, The use of mRNA display to select high-affinity protein-binding peptides. *Proc. Natl. Acad. Sci.* (2001), doi:10.1073/pnas.061028198.
6. G. T. Hermanson, in *Bioconjugate Techniques* (2013).

7. V. Singh, S. Wang, E. T. Kool, Genetically encoded multispectral labeling of proteins with polyfluorophores on a DNA backbone. *J. Am. Chem. Soc.* (2013), doi: 10.1021/ja4004393.

8. B. A. R. Williams, J. C. Chaput, Synthesis of peptide-oligonucleotide conjugates using a heterobifunctional crosslinker. *Curr. Protoc. Nucleic Acid Chem.* (2010), doi:10.1002/0471142700.nc0441s42.

What is claimed is:

1. A method of detecting an interaction between a macromolecule and an interaction partner, the method comprising:
   obtaining a composition comprising a plurality of macromolecules and a plurality of candidate interaction partners;
   performing two or more iterations of split-and-pool barcoding, each iteration comprising:
      (i) randomly distributing the composition into a plurality of partitions in fluid isolation from each other;
      (ii) in the plurality of partitions, barcoding the plurality of macromolecules and the plurality of candidate interaction partners with a combinatorial barcode unit,
         wherein within each partition, the plurality of macromolecules and the plurality of candidate interaction partners are barcoded with the same combinatorial barcode unit,
         wherein the plurality of macromolecules and the plurality of candidate interaction partners of different partitions receive different combinatorial barcode units from each other
         wherein a macromolecule and a candidate interaction partner that interact will assort together in a partition of the plurality of partitions; and
      (iii) pooling the barcoded plurality of macromolecules and the barcoded plurality of candidate interaction partners comprising the different combinatorial barcode units from the plurality of partitions into a single composition,
   wherein, after the two or more iterations of split-and-pool barcoding, each macromolecule of the plurality of macromolecules and each candidate interaction partner of the plurality of candidate interaction partners comprises a combinatorial barcode comprising two or more combinatorial barcode units, each combinatorial barcode unit corresponding to an iteration of split-and-pool-barcoding; and
   obtaining identifying information from the combinatorial barcodes of the plurality of macromolecules and the plurality of candidate interaction partners, wherein the identifying information permits detecting an interaction between a macromolecule of the plurality of macromolecules and a candidate interaction partner of the plurality of candidate interaction partners through the two or more iterations of split-and-pool barcoding,
   wherein a probability of the interaction between the macromolecule and the candidate interaction partner as being bona fide is proportional to the number of iterations of split-and-pool barcoding.

2. The method of claim 1, wherein each macromolecule of the plurality of macromolecules is a protein, and wherein each macromolecule of the plurality of macromolecules comprises an identifier barcode comprising a polynucleotide comprising a coding sequence of the respective macromolecule.

3. The method of claim 2, wherein the identifier barcode further comprises a covalent polypeptide tag fused to the polynucleotide, and wherein each macromolecule of the plurality of macromolecules further comprises a counterpart polypeptide covalently bound to the polynucleotide.

4. The method of claim 3, wherein the counterpart polypeptide is disposed at an N-terminal region of the protein.

5. The method of claim 4, wherein each macromolecule of the plurality of macromolecules comprising the identifier barcode is made according to a method comprising:
   fusing the covalent polypeptide tag to the polynucleotide;
   translating the polynucleotide in vitro, thereby producing the macromolecule comprising the counterpart polypeptide disposed at an N-terminal portion of the macromolecule; and
   covalently binding the polypeptide tag to the counterpart polypeptide, thereby making the macromolecule comprising the identifier barcode.

6. The method of claim 3, wherein the covalent polypeptide tag and counterpart polypeptide comprise a split CnaB protein; or a Spytag and SpyCatcher; or Isopeptag and pilin-C; or SnoopTag and SnoopCatcher; or DogTag and SnoopTagJr; or SdyTag and SdyCatcher.

7. The method of claim 3, wherein the covalent polypeptide tag is fused to the polynucleotide via a HUH protein, SMCC linkage, or RepB replicase.

8. The method of claim 2, wherein the identifier barcode further comprises a random oligonucleotide barcode of at least 5 nucleotides.

9. The method of claim 2, wherein the identifier barcode further comprises a terminal single-stranded handle sequence, and wherein each combinatorial barcode unit comprises a terminal single-stranded complement of the terminal handle sequence, wherein said barcoding comprises:
   permitting the terminal single-stranded handle sequences to anneal to the terminal single-stranded complement of a combinatorial barcode unit; and
   ligating the terminal handle sequences to the terminal single-stranded complement of the combinatorial barcode unit.

10. The method of claim 1, wherein the combinatorial barcode units comprise oligonucleotides, wherein different sequences of the oligonucleotides differentiate different combinatorial barcode units from each other; or
   wherein the combinatorial barcode units comprise detectable moieties, wherein different detectable moieties differentiate different combinatorial barcode units from each other.

11. The method of claim 2, further comprising sequencing the coding sequence of the macromolecule.

12. The method of claim 1, wherein the plurality of macromolecules are of a library of in vitro translated polypeptides.

13. The method of claim 1, wherein the plurality of macromolecules are selected from the group consisting of proteins, RNA binding proteins, antigen binding proteins, antibodies or fragments thereof, scFvs, nanobodies, and aptamers, or a combination of two or more of any of the listed items.

14. The method of claim 1, wherein the candidate interaction partners are selected from the group consisting of: proteins, peptides, RNAs, DNAs, and small molecules, or a combination of two or more of any of the listed items.

15. The method of claim 1, wherein the composition comprises at least $10^3$ different macromolecules and at least $10^3$ different candidate interaction partners.

16. The method of claim 1, further comprising detecting the interaction between the macromolecule and the candidate interaction partner, detecting an interaction between the macromolecule and a second candidate interaction partner, and detecting a lack of an interaction between the macromolecule, the candidate interaction partner, and the second candidate interaction partner, thereby indicating that the second candidate interaction partner has a probability of interfering with the interaction between the macromolecule and the candidate interaction partner.

17. The method of claim 1, further comprising detecting the interaction between the macromolecule and the candidate interaction partner, detecting an interaction between a second macromolecule and the candidate interaction partner, and detecting a lack of an interaction between the macromolecule, the second macromolecule, and the candidate interaction partner, thereby indicating that the second macromolecule has a probability of interfering with the interaction between the macromolecule and the candidate interaction partner.

18. The method of claim 1, comprising at least 3 iterations of split-and-pool barcoding.

* * * * *

```
                            SEQUENCE LISTING

<160> NUMBER OF SEQ ID NOS: 5

<210> SEQ ID NO 1
<211> LENGTH: 16
<212> TYPE: PRT
<213> ORGANISM: Artificial Sequence
<220> FEATURE:
<223> OTHER INFORMATION: Synthetic; isopeptag

<400> SEQUENCE: 1

Thr Asp Lys Asp Met Thr Ile Thr Phe Thr Asn Lys Lys Asp Ala Glu
1               5                   10                  15

<210> SEQ ID NO 2
<211> LENGTH: 13
<212> TYPE: PRT
<213> ORGANISM: Artificial Sequence
<220> FEATURE:
<223> OTHER INFORMATION: Synthetic; SpyTag

<400> SEQUENCE: 2

Ala His Ile Val Met Val Asp Ala Tyr Lys Pro Thr Lys
1               5                   10

<210> SEQ ID NO 3
<211> LENGTH: 12
<212> TYPE: PRT
<213> ORGANISM: Artificial Sequence
<220> FEATURE:
<223> OTHER INFORMATION: Synthetic; SnoopTag

<400> SEQUENCE: 3

Lys Leu Gly Asp Ile Glu Phe Ile Lys Val Asn Lys
1               5                   10

<210> SEQ ID NO 4
<211> LENGTH: 23
<212> TYPE: PRT
<213> ORGANISM: Artificial Sequence
<220> FEATURE:
<223> OTHER INFORMATION: Synthetic; DogTag

<400> SEQUENCE: 4

Asp Ile Pro Ala Thr Tyr Glu Phe Thr Asp Gly Lys His Tyr Ile Thr
1               5                   10                  15

Asn Glu Pro Ile Pro Pro Lys
            20

<210> SEQ ID NO 5
<211> LENGTH: 13
<212> TYPE: PRT
<213> ORGANISM: Artificial Sequence
<220> FEATURE:
<223> OTHER INFORMATION: Synthetic; SdyTag

<400> SEQUENCE: 5

Asp Pro Ile Val Met Ile Asp Asn Asp Lys Pro Ile Thr
1               5                   10
```